United States Patent [19]

Samson

[11] Patent Number: 5,415,632
[45] Date of Patent: May 16, 1995

[54] BREAST PUMP

[75] Inventor: Ilan Samson, London, England

[73] Assignee: Playskool, Inc., Pawtucket, R.I.

[21] Appl. No.: 179,378

[22] Filed: Jan. 10, 1994

[51] Int. Cl.⁶ .......................... A61M 1/06; A61F 5/44
[52] U.S. Cl. .......................................... 604/74; 604/346
[58] Field of Search .................................... 604/73–75, 604/316, 319, 327, 346

[56] References Cited

U.S. PATENT DOCUMENTS

| | | |
|---|---|---|
| 790,051 | 5/1905 | Halstead . |
| 897,289 | 9/1908 | Howell . |
| 1,484,874 | 2/1924 | Del Castillo . |
| 1,509,226 | 9/1924 | Brown .................................. 604/74 |
| 2,419,795 | 4/1947 | Saunders . |
| 3,782,385 | 1/1974 | Loyd ..................................... 604/74 |
| 4,263,912 | 4/1981 | Adams . |
| 4,311,141 | 1/1982 | Diamond . |
| 4,323,067 | 4/1982 | Adams . |
| 4,400,168 | 8/1983 | Buechel et al. . |
| 4,583,970 | 4/1986 | Kirchner .............................. 604/74 |
| 4,813,932 | 3/1989 | Hobbs .................................. 604/74 |
| 4,857,051 | 8/1989 | Larsson ................................ 604/74 |
| 4,892,517 | 1/1990 | Yuan et al. ........................... 604/74 |
| 4,983,634 | 1/1991 | Corby . |
| 5,009,638 | 4/1991 | Riedweg et al. ..................... 604/74 |

FOREIGN PATENT DOCUMENTS 762701 5/1957 United Kingdom .
2082920 3/1982 United Kingdom .
2127293 4/1984 United Kingdom .

Primary Examiner—C. Fred Rosenbaum
Assistant Examiner—Frank Wilkens, III
Attorney, Agent, or Firm—Kurt R. Benson

[57] ABSTRACT

An ergonomically effective breast pump includes a pump body including a breast engaging portion, a breast milk receiving container on the pump body, a one-way valve between the pump body and the container and a piston and cylinder assembly for applying vacuum to the interior of the pump body. The breast engaging portion is receivable in engagement with a breast of a user, and the piston and cylinder assembly includes a piston which is moveable in a cylinder in a direction outwardly and away from the user for applying vacuum to the breast of the user through the pump body. The breast pump further includes a thumb receiving element for moving the piston in the cylinder in a direction outwardly and away from the user with a thumb on a hand of the user, a handle element receivable in the same hand for assisting the user to draw the piston in an outward direction in the cylinder and a spring element for returning the piston in a direction toward the user.

9 Claims, 3 Drawing Sheets

BREAST PUMP

BACKGROUND AND SUMMARY OF THE INVENTION

The instant invention relates a maternity apparatus and more particularly to an effective, self-operated, manual breast pump for a mother of a young infant.

It is well recognized that mother's milk is preferable to other foods, such as cow's milk or various feeding formulas for feeding infants. However, it is also well recognized that it is often not practical for mothers to breast feed their infant children over prolonged periods of time. As a result, various types of pumping devices have been heretofore developed for extracting mother's milk from the breasts of mothers of young children.

A number of different types of devices, including both electrical and manual breast pumps, have been heretofore available for extracting mother's milk from the breasts of women. In this regard, however, electrically operated breast pumps which operate on standard house current have generally been found to be impractical as being costly and awkward to transport. Battery-powered electrical pumps have also been found to be costly, and they have generally been found to be less effective than other types of breast pumps. As a result, even though many of the heretofore available hand operated pumps have been found to be awkward and tedious to use, they have generally been found to be less costly and more practical than electrically operated breast pumps.

Manually operated breast pumps representing closest prior to the subject invention of which the applicant is aware are disclosed in the U.S. Patent to Halstead, U.S. Pat. Nos. 790,051; Howell No. 897,289; Del Castillo, 1,484,874; Brown, 1,509,226; Saunders, 2,419,795; Loyd, 3,782,385; Adams 4,263,.912; Adams, 4,323,067; Diamond 4,311,141; Buechel et al, 4,400,168; Kirchner 4,583,970; Hobbs 4,813,932; Yuan et al, 4,892,517; Corby 4,983,634 and Riedwegetal, 5,009,638 and the British patents Nos. 762,701; 2,082,920; 2,127,293. However, while these references disclose a wide variety of different manually operated devices, they fail to provide a simple breast pump which is practical, relatively inexpensive to the manufacture and easy to operate.

The instant invention provides a highly effective breast pump which is effective and easy to operate for extracting mother's milk from the breasts of a woman and which is also adapted to be constructed at a relatively low cost. Specifically, the instant invention provides an effective self-operated breast pump which is adapted for easy and effective single-handed operation. Still more specifically, the instant invention provides a breast pump comprising a pump body including a breast engaging portion which faces in a first direction, a base portion, a breast milk receiving container on the base portion and a one way valve between the pump body and the container. The breast pump further includes a piston and cylinder assembly comprising a cylinder which communicates with the interior of the pump body, a piston in the cylinder and a seal between the piston and the cylinder. The piston and cylinder assembly is arranged so that the piston is movable in the cylinder in a second direction which is substantially opposite to the first direction for applying a vacuum to the interior of the pump body. The piston includes a thumb receiving element for moving the piston in the second direction in the cylinder, and the pump further includes a handle on the pump body which is adapted to be received in a hand of a user for drawing the piston in the second direction using a thumb on the same hand which is received in the thumb receiving element. The handle preferably includes a fixed handle element which extends in substantially perpendicular relation to the second direction and which is normally spaced from the thumb receiving element so that the handle element can be effectively utilized for enabling a user to draw the piston in the second direction with a thumb on the users hand received in the thumb receiving element. The breast pump preferably further comprises a resiliently bendable elongated band which is operative for resiliently biasing the piston in substantially the first direction in the cylinder with a relatively light, substantially uniform biasing force. The resilient band is constructed so that it is movable from first reduced partially bent position to a second increased partially bent position during movement of the piston from a forward first position in the cylinder to a rearward second position therein. Further, the piston is preferably dimensioned so that it is normally spaced from the side wall of the cylinder, and it is normally guided in its travel in the cylinder by the seal which extends between the piston and the cylinder and the thumb ring by which it is pulled.

It has been found that the breast pump of the instant invention can be effectively operated for extracting milk from a breast of a female user. Specifically, it has been found that because the breast pump includes a piston and cylinder assembly comprising a piston which is directly moveable in a direction away from an operator with a thumb on a hand of the operator by drawing the thumb toward a handle element, the piston and cylinder assembly can be simply and easily operated for extracting mother's milk from a breast of the operator. In this regard, because the device is operated by merely drawing the thumb receiving element toward the handle element by moving a thumb on a hand of the operator toward the fingers on the same hand, the device can be comfortably operated for reciprocating the piston in the cylinder to extract mother's milk from a breast of the operator. Further, because the breast pump includes a resilient spring element which is operative for biasing the piston in the first direction with a substantially constant biasing face, the amount of resistance to movement of the piston in the second direction by an operator of the device can be maintained at a minimal level to enable the device to be even more easily manipulated by the operator. Still further, because the handle element is positioned in substantially perpendicular relation to the direction in which the breast engaging portion faces, the handle element can be more easily and comfortably grasped by an operator during use of the device.

Accordingly, it is primary object of the instant invention to provide a self-operated breast pump which is adapted for comfortable, single-handed operation.

Another object of the instant invention is to provide an effective breast pump which is easy to manipulate for extracting mother's milk from a breast of an operator.

An even still further object of the instant invention is provide a breast pump comprising a cylinder and a piston which is movable in the cylinder by directly moving the piston in a direction outwardly and away from the operator for applying a vacuum to a breast of the operator.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention.

DESCRIPTION OF THE INVENTION

Figure 1:
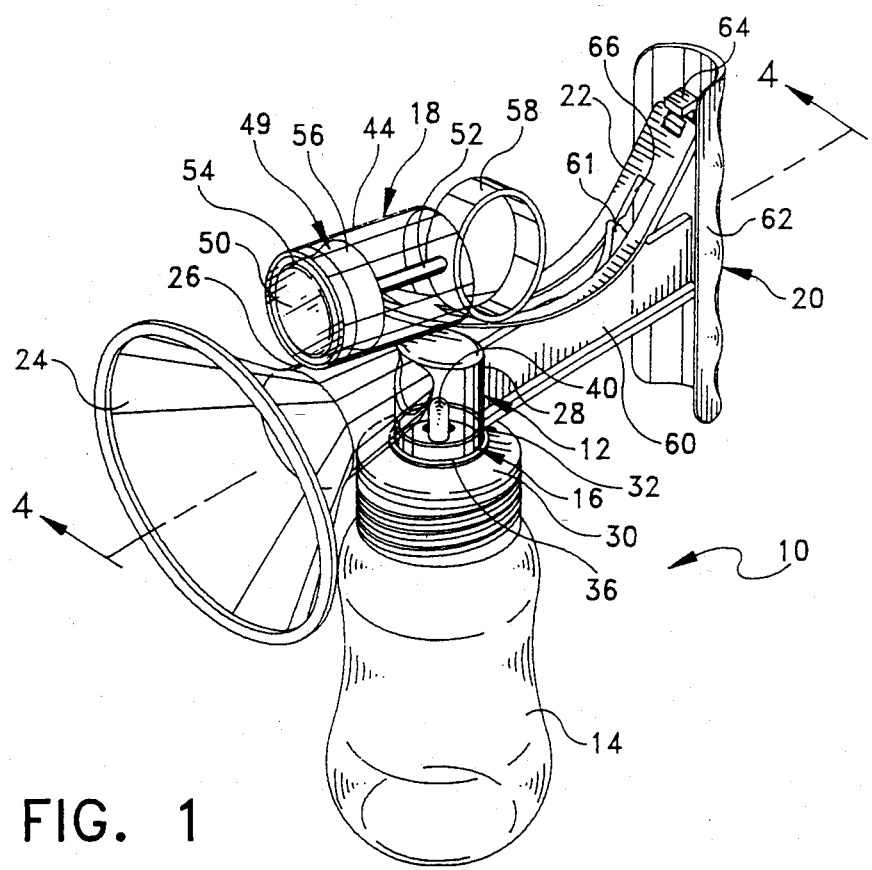
FIG. 1 is a perspective view of the breast pump of the instant invention with the piston in the first position thereof.
Figure 2:
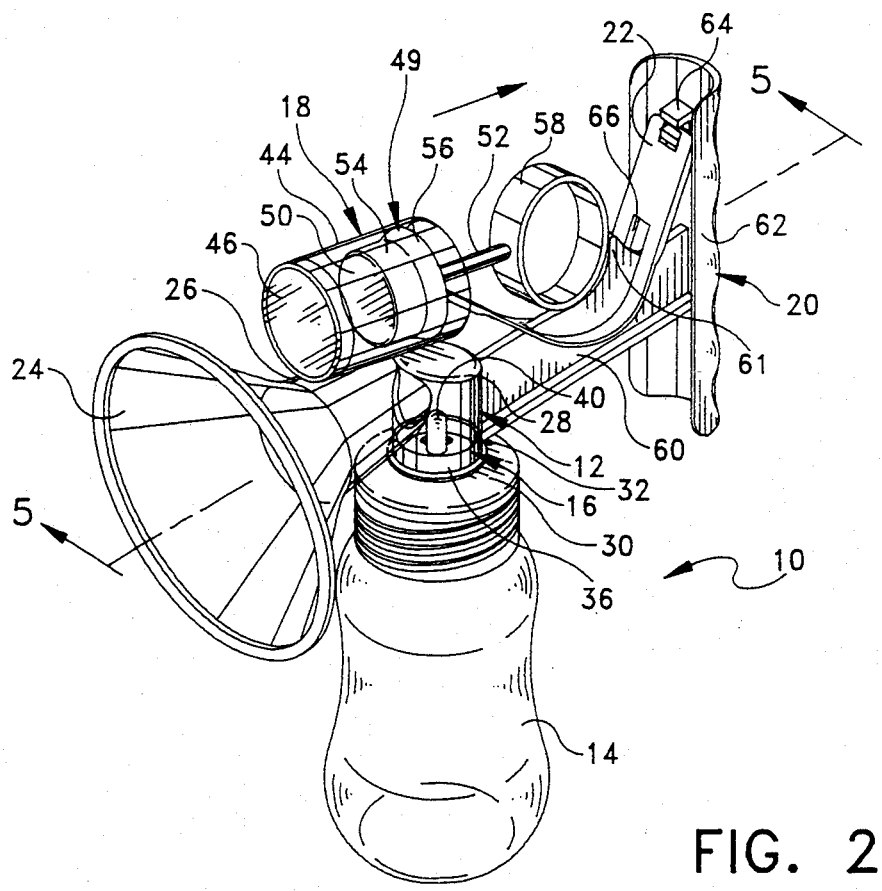
FIG. 2 is a similar perspective view with the piston in the second position thereof.

Referring now to the drawings, the breast pump of the instant invention is illustrated and generally indicated at 10 in FIGS. 1 through 5. The breast pump 10 comprises a pump body generally indicated at 12, a breast milk receiving container 14, a valve assembly generally indicated at 16 between the pump body 12 and the container 14, a piston and cylinder assembly generally indicated at 18 on the pump body 12, a handle assembly generally indicated at 20 and a biasing element 22. The breast pump 10 is adapted to be held against a breast of an operator utilizing a hand of the operator while the same hand is operated for manipulating the piston and cylinder assembly 18 to apply a vacuum to the interior of the pump body 12. Accordingly, the pump 10 can be utilized for drawing mother's milk into the interior of the pump body 12 so that the mother's milk can be passed downwardly through the valve assembly 16 and into the container 14 when the vacuum is released in the interior of the pump body 12.

The pump body 12 is preferably integrally molded from a suitable plastic material, and it includes a conical or funnel-shaped breast engaging portion 24, a central tubular portion 26, which extends from the breast engaging portion 24, and a base portion 28 which extends downwardly from the tubular portion 26. The breast engaging portion 24 is adapted to be received in engagement with a breast of an operator so that the nipple on the breast is directed into the tubular portion 26. The base portion 28 extends downwardly from the tubular portion 26, and it merges into a threaded cap portion 30 around an opening 31. The cap portion 30 is adapted to be received in threaded engagement on the container 14, and it has a vent opening 32 therein for venting air from the container 14 as mother's milk is accumulated therein.

The container 14 is preferably integrally molded from a suitable transparent plastic material, and it includes a threaded upper neck portion 34 which is adapted to be received in threaded engagement in the cap portion 30.

The valve assembly 16 is operative for maintaining a vacuum in the pump body portion 12 as the piston and cylinder assembly 18 is operated to produce a vacuum therein, but it is nevertheless adapted to permit mother's milk to pass into the container 14 when the pressure in the pump body 12 is normalized, i.e. returned to at least ambient pressure. Accordingly, the valve assembly 16 is operative as a one way valve which enables mother's milk to be drawn from a breast of a user and accumulated in the container 14. The valve assembly 16 comprises a circular cap portion 36 which is adapted to be releasably retained in frictional engagement in the opening 31. The cap portion 36 has a plurality of openings 38 formed therein, and it includes a downwardly extending retaining lug 39 and a push-out pin 40 which projects upwardly from the center of the cap portion 36. The valve assembly 16 further comprises a circular elastomeric diaphragm element 42 which is received on the retaining lug 39 for releasably retaining it engagement with the underside of the disk 36 so that the diaphragm element 42 normally covers the openings 38. Accordingly, when a vacuum is applied to the interior of the pump body 12, the diaphragm 42 element is drawn against the underside of the cap 36 to sealingly obstruct the openings 38. However, when vacuum is released from the interior of the pump body 12 and the pressure therein is atmospheric or greater, liquid, such as mother's milk, can pass downwardly through the openings 38 and between the diaphragm 42 and the underside of the cap 36 so that the liquid gravitates or is pushed into the container 14.

The piston and cylinder assembly 18 comprises a cylinder portion 44 having a closed front end wall 46. The cylinder portion 44 is open at the rear end thereof, and a reduced aperture or passage 48 extends between the interior of the cylinder portion 44 and the interior of the pump body 12. Also included in the piston and cylinder assembly 18 is a piston element 49 including a piston head 50, having a rearwardly extending piston stem 52 thereon, and a seal 54 on the piston head. The piston head 50 is dimensioned to be loosely received in the cylinder portion 44, and the seal 54 is received on the piston head 50 so that it normally maintains the piston head 50 in spaced, but sealed, relation to the inner wall of the cylinder portion 44. The seal 54 is of cup-shaped configuration, and it includes a sealing rim 56 which is adapted to sealing engage the inner wall of the cylinder 44 in a manner which permits the piston head 50 to travel back and forth in the interior of the cylinder portion 44. In this regard, the piston head 50 is normally guided solely by the seal 54 as the piston head 50 travels in the cylinder portion 44. As a result, it is not normally possible for the piston rod to pivot on other guide means which might cause the piston head 50 to be urged against the wall along one side of the cylinder portion 44 and thereby cause the seal 54 to be partially separated from the opposite side of the wall of the cylinder portion 44. The piston stem 52 has a reduced aperture 57 therein adjacent the piston head 50 and the piston element 49 further comprises a thumb ring 58 which is received on the rear end of the piston stem 52. As illustrated, the components of the piston element 49, i.e. the piston head 50, the piston stem 52, and the thumb ring 58, and the cylinder portion 44 are dimensioned to permit the piston element 49 to be reciprocally moved between the first or forward position illustrated in FIGS. 1 and 4 and the second or rearward position illustrated in FIGS. 2 and 5. Accordingly, when the breast engaging portion 24 is received in engagement with a breast of a user and the piston head 50 is drawn rearwardly in the cylinder portion 44 from the first or forward position thereof to the second or rearward position thereof, a vacuum is applied to the interior of the cylinder portion 44 which is communicated to the interior of the pump body 12 through the passage 48 for extracting mother's milk from the user's breast.

The handle element 20 includes a base portion 60 which extends outwardly from the pump body 12 in a direction substantially opposite to that of the breast engaging portion 24. The handle element 20 further comprises a spring retainer portion which extends upwardly from the base portion 60 and a handle portion 62 which extends substantially perpendicularly upwardly from the base portion 60, the handle portion 62 having an inwardly facing spring clip 64 thereon. The handle portion 62 is formed in an elongated generally rounded configuration, and it is adapted to be comfortably received in a hand of a user so that the fingers on the hand are at least partially wrapped around the handle portion 62. As will be readily apparent, when the handle portion 62 is received in a hand of a user in this manner, the thumb on the same hand is readily receivable in the thumb ring 58 for drawing the piston head 50 rearwardly in the cylinder portion 44 with a simple and easy squeezing action. As will also be apparent, the construction and orientation of the piston element 49 enable the piston element 49 to be drawn rearwardly by a natural ergonomically favorable thumb movement in which the thumb ring 58 is drawn along a constrained path which keeps the piston element 49 generally aligned with the axis of movement thereof. The size and configuration of the seal 54 and the absence of other means for guiding the piston element 49 allows moderate deviations in the orientation of the piston element 49 without affecting the seal between the seal 54 and the wall of the cylinder 44

Figure 3:
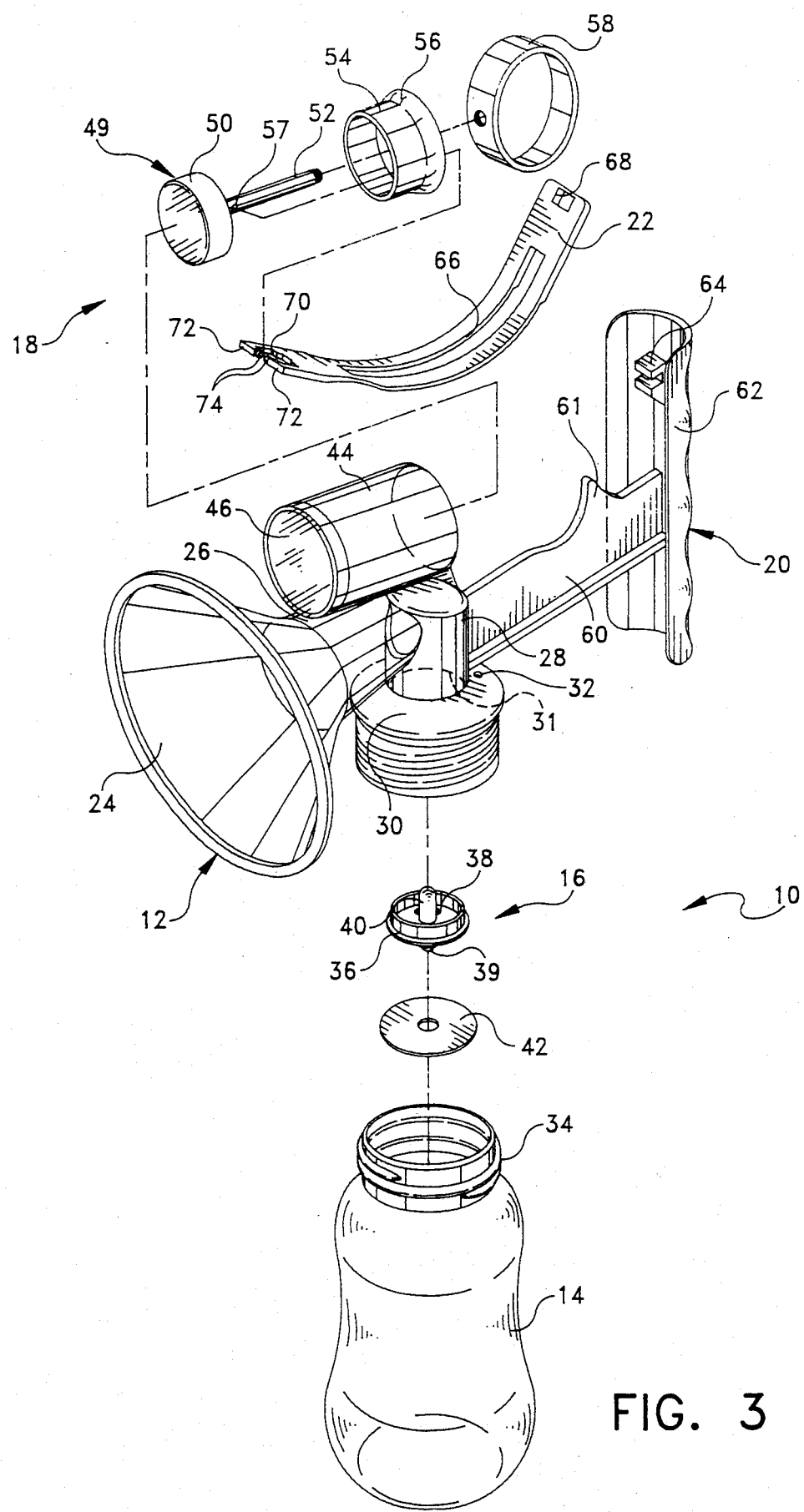
FIG. 3 is an exploded perspective view of the breast pump.
Figure 4:
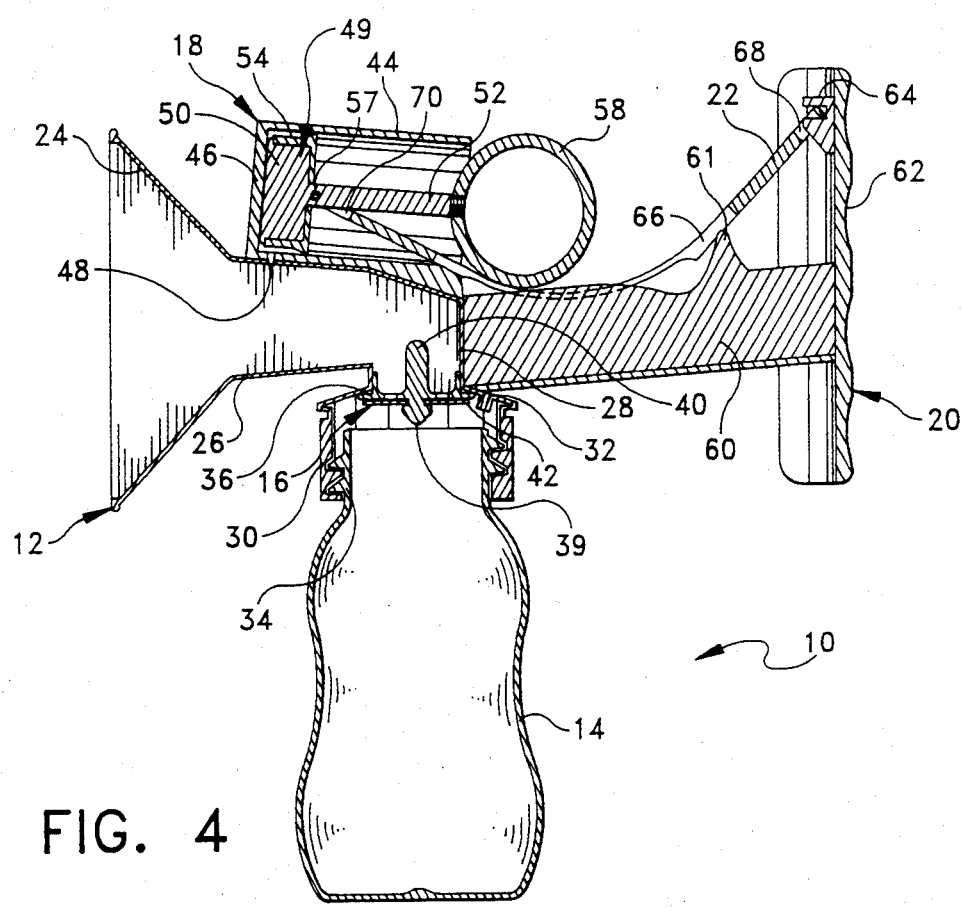
FIG. 4 is a sectional view taken along line 4—4 in FIG. 1.
Figure 5:
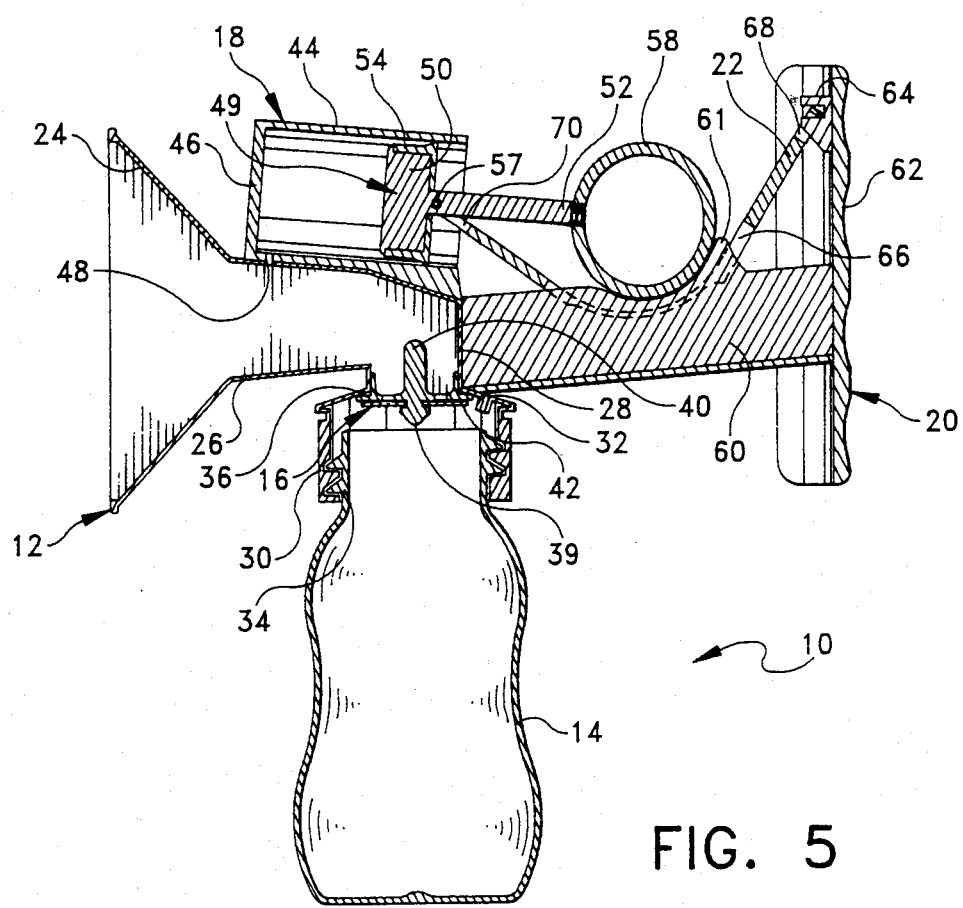
FIG. 5 is a sectional view taken along line 5—5 in FIG. 2.

The spring element 22 is illustrated most clearly in FIG. 3, and it is operative for biasing the piston head 50 to the forward or first position thereof in the cylinder 44 as illustrated in FIGS. 1 and 4. The spring element 22 has an elongated longitudinally extending guide slot 66 formed therein, and it has a rectangular aperture 68 formed therein adjacent one end thereof. The spring element 22 has an opening 70 formed therein at the opposite end thereof which defines a pair of inwardly extending retaining arms 72 having opposed terminal pins 74 thereon. The spring element 22 is assembled in the pump 10 so that the pins 74 are received in opposite ends of the aperture 57 in the piston stem 52, and so that the retaining projection 61 is received in the slot 66. The spring element 22 is further assembled so that the aperture 68 is received in the spring clip 64 to retain the spring element 22 in a partially bent position, wherein it extends between the handle portion 62 and the piston stem 52. As will be seen, the spring element 22 is dimensioned so that when it is in the first position thereof illustrated in FIG. 1, the spring element 22 is in a first partially bent disposition, and so that when the piston head 50 is drawn rearwardly to the position illustrated in FIG. 2, the spring element 22 is moved into a second further partially bent disposition. However, because of the overall length of the spring element 22 and the extent of the possible travel of the piston head 50 in the cylinder 44 the spring element 22 is not permitted to either reach a substantially straight disposition or a sharply bent disposition. As a result, the forward biasing force applied by the spring element 22 to the piston head 50 is substantially constant or uniform throughout the travel of the piston head 50 in the cylinder portion 44. Accordingly, the amount of force required to draw the piston head 50 rearwardly in the cylinder 44 does not normally increase significantly as the piston head 50 travels rearwardly in the cylinder portion 44, and it is relatively easy for an operator to draw the piston head 50 rearwardly against the force of the spring element 22. Nevertheless, the spring element 22 is capable of effectively returning the piston head 50 to a forward position in the cylinder portion 44.

Accordingly, for use in operation of the breast pump 10 the breast engaging element 24 is positioned in engagement with a breast of a user so that the nipple on the breast is directed into the tubular portion 26. The handle element 20 is then grasped with the fingers on a hand of the user, and a thumb on the same hand is passed through the thumb ring 58. The thumb ring 58 is then drawn toward the handle portion 62 by drawing the thumb on the operator's hand toward the fingers thereon. By operating the pump 10 in this manner it is possible to apply a sufficient level of vacuum to the interior of the pump body 12 to draw mother's milk from the operator's breast so that the milk passes into the tubular portion 26. Further, by thereafter releasing the piston head 50 so that it is returned to its initial forward position in the cylinder portion 44, the vacuum in the pump body 12 is released, the pressure in the pump body returns to atmospheric pressure or greater, and the extracted milk passes through the valve assembly 16 and into the container 14. Still further, by then repeating this entire operation a plurality of times, it is possible to apply and release vacuum in the interior of the pump body 12 in a pulsating fashion which causes milk to be repeatedly extracted from the breast as vacuum is applied thereto and released and which allows the extracted milk to pass into the container 14 through the seal element 16. In this regard, at the same time, the vent hole 32 releases pressure from the interior of the container 14 when the pressure in the pump body 12 exceeds atmospheric pressure.

It is seen therefore that the instant invention provides an effective breast pump for extracting milk from a female breast. In this regard, the piston and cylinder assembly 18, the handle element 20 and spring element 22 are positioned so that an operator of the device 10 can effectively and easily repeatedly draw the piston head 50 rearwardly in the cylinder portion 44 for applying suction to the pump body portion 12. Specifically, the piston and cylinder assembly 18, the handle element 20 and the spring element 22 are constructed and oriented so that the piston and cylinder assembly 18 can be easily operated by drawing the piston head 50 an outward direction relative to a breast of an operator. This enables the operator to comfortably operate the device 10 without requiring awkward manipulations, such as bending the wrist backwards or the application of excessive force to the piston head 50. Further, because the spring element 22 applies a substantially uniform or constant biasing force to the piston element 49 throughout the travel thereof, and because the device 10 is operative without pivoting levers and the like, an operator of the device 10 can more effectively operate the piston and cylinder assembly 18 so as to repeatedly reciprocate the piston head 50 in the cylinder portion 44 over an extended period of time. Still further, because the piston head 50 is guided in its movement in the cylinder portion 44 solely by the rim portion 56 of the seal 54, the seal 54 is normally maintained in uniform pressurized engagement with the inner wall of the cylinder portion 44 around the entire circumference of the rim portion 56, and it cannot normally be moved away from the inner wall as a result of the engagement of the piston stem 52 with other guide means. Hence it is seen, that the breast pump of the instant invention represents a significant improvement in the related art which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A breast pump comprising:
   a. a pump body having an interior and including a breast engaging portion facing in a first direction and a base portion;
   b. a breast milk receiving container on said base portion;
   c. one way valve means between said base portion and said container for alternatively maintaining a vacuum in said pump body or allowing breast milk to pass into said container;
   d. a piston and cylinder assembly on said pump body, said piston and cylinder assembly including a cylinder communicating with the interior of said pump body, a piston in said cylinder and seal means between said piston and said cylinder, said piston being moveable in said cylinder in a second direction which is substantially opposite to said first direction for applying vacuum to the interior of said pump body, said piston and cylinder assembly including a thumb receiving element which is directly connected to said piston said thumb receiving element being moveable in said second direction for directly moving said piston in said second direction in said cylinder; and
   e. handle means on said pump body adapted to be received in a hand of a user for moving said piston in said second direction with a thumb on the same hand received in said thumb receiving element.

2. In the breast pump of claim 1, said piston being normally spaced from said cylinder and being guided in its travel therein in said second direction solely by said seal mens and said thumb receiving elements.

3. A breast pump comprising:
   a. a pump body having an interior and including a breast engaging portion facing in a first direction and a base portion;
   b. a breast milk receiving container on said base portion;
   c. one way valve means between said base portion and said container for alternatively maintaining a vacuum in said pump body or allowing breast milk to pass into said container;
   d. a piston and cylinder assembly on said pump body, said piston and cylinder assembly including a cylinder communicating with the interior of said pump body, a piston in said cylinder and seal means between said piston and said cylinder, said piston being moveable in said cylinder in a second direction which is substantially opposite to said first direction for applying vacuum to the interior of said pump body, said piston including a thumb receiving element for moving said piston in said second direction in said cylinder; and
   e. handle means on said pump body adapted to be received in a hand of a user for moving said piston in said second direction with a thumb on the same hand received in said thumb receiving element, said handle means including a fixed handle element which extends in substantially perpendicular relation to said second direction.

4. In the breast pump of claim 3, said handle element being normally spaced from said thumb receiving element in said second direction.

5. The breast pump of claim 3 further comprising biasing means biasing said piston in substantially said first direction in said cylinder.

6. In the breast pump of claim 5, said piston traveling in said second direction from a first position in said cylinder to a second position therein for applying vacuum to said pump body interior, said biasing means biasing said piston with a substantially constant biasing force during movement of said piston between said first and second positions.

7. In the breast pump of claim 6, said biasing means comprising a resiliently bendable elongated band, said band moving from a first reduced partially bent position thereof to a second increased partially bent position thereof during movement of said piston from the first position thereof to the second position thereof.

8. In the breast pump of claim 6, said handle means being spaced from said thumb receiving element when said piston is in the first position thereof.

9. A breast pump comprising:
   a. a pump body having an interior and including a breast engaging portion facing in a first direction and a base portion;
   b. a breast milk receiving container on said base portion;
   c. one way valve means between said base portion and said container for alternatively maintaining a vacuum in said pump body or allowing breast milk to pass into said container;
   d. a piston and cylinder assembly on said pump body, said piston and cylinder assembly including a cylinder communicating with the interior of said pump body, a piston in said cylinder and seal means between said piston and said cylinder, said piston being moveable in said cylinder in a second direction which is substantially opposite to said first direction for applying vacuum to the interior of said pump body, said pump body including a tubular portion between said breast engaging portion and said base portion, said base portion depending from said tubular portion, said cylinder being disposed above said tubular portion in substantially parallel relation thereto, said piston including a thumb receiving element for moving said piston in said second direction in said cylinder; and
   e. handle means on said pump body adapted to be received in a hand of a user for moving said piston in said second direction with a thumb on the same hand received in said thumb receiving element.

* * * * *